US012622864B2

(12) United States Patent
Oliveira et al.

(10) Patent No.: US 12,622,864 B2
(45) Date of Patent: May 12, 2026

(54) AQUEOUS CONDITIONING COSMETIC COMPOSITION, COSMETIC PRODUCTS, METHOD OF REPAIR AND PROTECTION OF HAIR PROPERTIES, AND, USE OF A COSMETIC PRODUCT

(71) Applicant: Oxiteno S.A. Indústria e Comércio, São Paulo (BR)

(72) Inventors: Vicente Gomes Oliveira, Mauá (BR); Jacqueline Moreira De Morais, Mauá (BR); Camila de Fátima Oliveira, Mauá (BR); Rafaela Pepineli, Mauá (BR); Talison Alvarenga Dos Santos, Mauá (BR); André Oliva De Palma, Mauá (BR); Cristiane Aparecida Furtado Canto, Mauá (BR)

(73) Assignee: Oxiteno S.A. Indústria e Comércio, São Paulo (BR)

( * ) Notice: Subject to any disclaimer, the term of this patent is extended or adjusted under 35 U.S.C. 154(b) by 492 days.

(21) Appl. No.: 18/013,019

(22) PCT Filed: Apr. 15, 2021

(86) PCT No.: PCT/BR2021/050157

§ 371 (c)(1),
(2) Date: Dec. 27, 2022

(87) PCT Pub. No.: WO2022/000057

PCT Pub. Date: Jan. 6, 2022

(65) Prior Publication Data

US 2023/0277433 A1 Sep. 7, 2023

(30) Foreign Application Priority Data

Jun. 29, 2020 (BR) ........................ 102020013361-6

(51) Int. Cl.

| | |
|---|---|
| ***A61K 8/39*** | (2006.01) |
| ***A61K 8/81*** | (2006.01) |
| ***A61K 8/86*** | (2006.01) |
| ***A61Q 5/00*** | (2006.01) |
| ***A61Q 5/02*** | (2006.01) |
| ***A61Q 5/12*** | (2006.01) |

(52) U.S. Cl.
CPC ................ *A61K 8/86* (2013.01); *A61Q 5/002* (2013.01); *A61Q 5/02* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

2018/0168997 A1* 6/2018 Hoffmann .............. A61K 8/898

FOREIGN PATENT DOCUMENTS

| | | |
|---|---|---|
| CN | 108635250 | 10/2018 |
| DE | 102007001019 | 7/2008 |
| EP | 1719546 | 11/2006 |
| EP | 2677990 | 1/2014 |
| KR | 10-2018-0063805 | 6/2018 |
| RU | 2734252 | 10/2020 |

OTHER PUBLICATIONS

Supplementary European Search Report and the European Search Opinion Dated Sep. 17, 2024 From the European Patent Office Re. Application No. 21833147.8. (8 Pages).
International Search Report and the Written Opinion Dated Jul. 20, 2021 From the International Searching Authority Re. Application No. PCT/BR2021/050157.
Invitation Pursuant to Rule 137(4) and Article 94(3) EPC Dated Oct. 30, 2025 From the European Patent Office Re. Application No. 21833147.8. (4 Pages).

* cited by examiner

*Primary Examiner* — Brian Gulledge

(57) ABSTRACT

The present invention relates to conditioning cosmetic compositions comprising, in a cosmetically acceptable aqueous medium, non-ionic surfactants and cationic polymers. In particular, these compositions are reserved for applications to hair with or without rinsing. In addition, the compositions concern methods of repair, protection, and improvement of hair properties. Additionally, the present invention relates to cosmetic products comprising such cosmetic compositions, such as shampoos, conditioners and hair treatment products, as well as the use thereof.

12 Claims, 1 Drawing Sheet

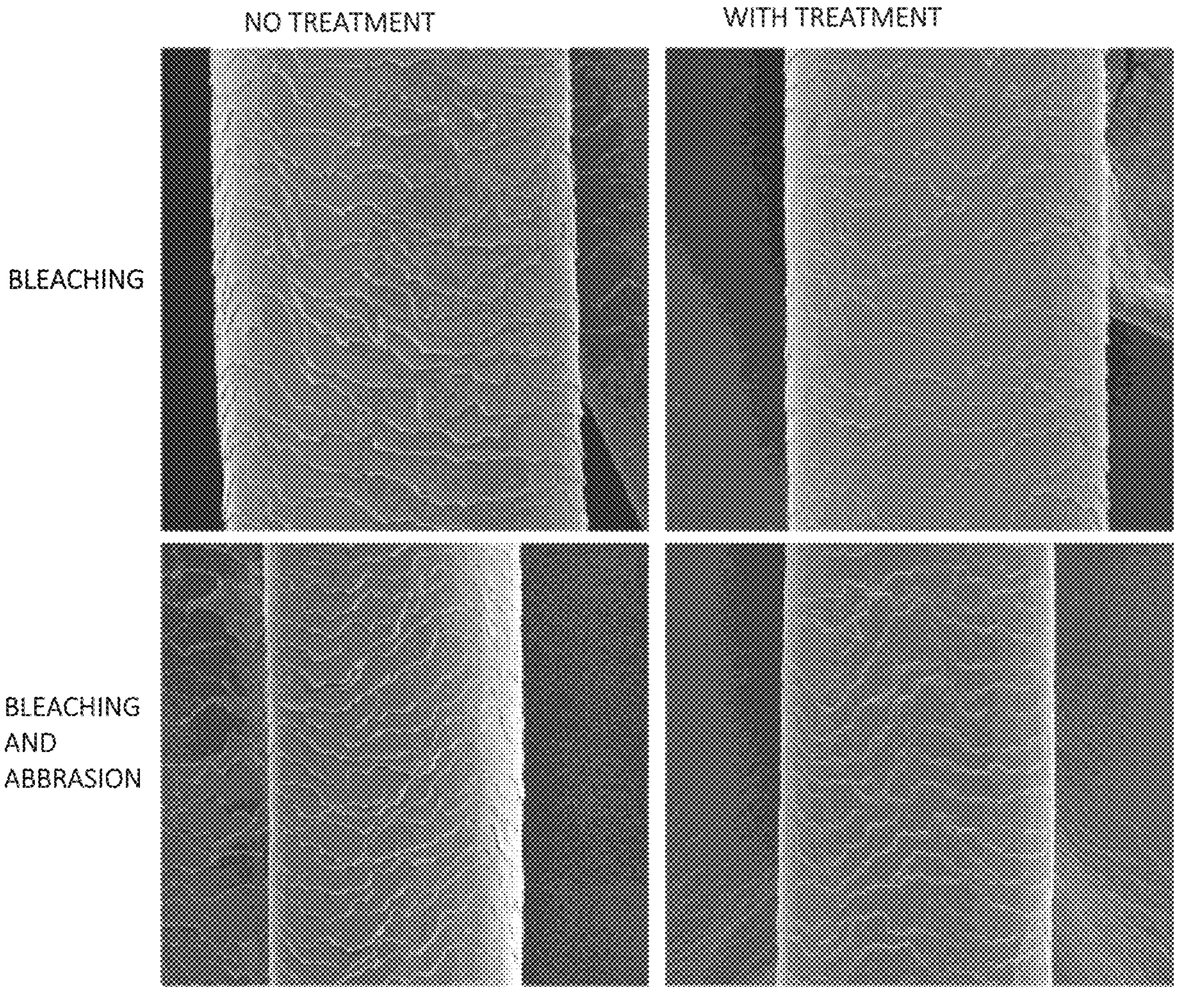
NO TREATMENT
WITH TREATMENT
BLEACHING
BLEACHING
AND
ABBRASION

AQUEOUS CONDITIONING COSMETIC COMPOSITION, COSMETIC PRODUCTS, METHOD OF REPAIR AND PROTECTION OF HAIR PROPERTIES, AND, USE OF A COSMETIC PRODUCT

FIELD OF THE INVENTION

The present invention relates to conditioning cosmetic compositions comprising, in a cosmetically acceptable aqueous medium, non-ionic surfactants and cationic polymers. In particular, these compositions are reserved for applications to hair with or without rinsing.

Additionally, the present invention relates to cosmetic products comprising such cosmetic compositions, such as shampoos, conditioners and treatment products.

In addition, the present invention deals with method of protection and repair of hair properties.

BACKGROUND OF THE INVENTION

Damage to hair can be caused by different aggressive sources, such as oxidative and reductive chemical treatments of bleaching, dyeing, perming and straightening; thermal treatments by use of flat irons, curling irons, and blow dryers; exposure to ultraviolet radiation and environmental pollution; mechanical sources of friction and abrasion, among others.

Typically, damage to the hair is manifested on the surface of the hair shafts, that is, in the cuticles; and with the loss of protein from its interior, that is, from the cortex, resulting in changes in macroscopic properties of hair's manageability (combability, tangling and stiffness), sensory attributes (softness and luster) and mechanical strength of the strands; as well as microscopic properties such as structural integrity and loss of the natural hydrophobicity of its surface.

Consumers who have damaged hair are usually not satisfied with the conditioning effect of conventional hair products. Such products sometimes deliver excessive conditioning (build-up) without adding in volume, sometimes deliver an insufficient light conditioning to ensure the appropriate restoration on the properties mentioned above. This is due to less interaction with the hydrophilic surfaces of damaged hair, leading to the removal of the ingredients during washing.

For the purpose of improving such properties of damaged hair, performance additives are added in cosmetic products. Traditionally, vegetable oils, emollient esters, amino acid derivatives, high molecular weight silicones, volatile silicones, cationic surfactants, cationic polymers, amphoteric polymers or anionic polymers are the groups of ingredients used for this purpose. The use of such groups of ingredients, as well as their combinations, is due to the predominant deposition and adhesion with the surface of the hair shafts, as well as the lubricity to the surface provided by them.

The state of the art contains a myriad of cationic polymers, applied alone and/or in commercial mixtures available for hair conditioning. There are also mixtures of cationic polymers with ionic surfactants and other components for emollient and wetting action, such as esters, glycerin, oils (mineral and vegetable) and other components known to those skilled in the art for the purpose of conditioning the hair.

However, although a variety of conditioning products is available on the market, there is a need to formulate products that obtain desirable effects not only related to restorative conditioning of hair due to the neutralization of negative hair charges, mechanism of action of cationic polymers, but also related to hair protection. In addition, many conditioning compositions in the literature restrict their application only to shampoos or conditioners, bringing complexity in the process of drawing up hair product lines.

U.S. Pat. No. 9,511,008B2 describes a hair conditioning method applying a rinse-free cosmetic composition comprising at least one alkyl ether alkylamine or a quaternary alkyl ether alkylamine, an aryl silicone and a polyquaternary cationic polymer or quaternary silicone, selected from the group consisting of polyquaternium-6, polyquaternium-10, polyquaternium-11, silicone quaternium-18 and silicone quaternium-22. Such a composition says it causes a greater hydrophobicity of the hair and promotes ease in combing, elasticity and volume of the hair.

The application US20120244100A1 describes an emollient agent and a process for improving the properties of damaged hair, comprising: (A) an ester compound of dipentaerythritol, and at least one fatty acid selected from the group consisting of fatty acids having 5 to 16 carbon atoms, and one or more substances selected from the group consisting of (B) an ester compound having a linear or branched alkyl or alkenyl group having 16 to 18 carbon atoms, and (C) an alcohol having a linear or branched alkyl or alkenyl group having 16 to 18 carbon atoms, and (D) a hydrocarbon having at least 20 carbon atoms. Said agent confers reduction of the feeling of roughness of damaged hair to provide a smooth feel, in addition to gloss retention, adhesiveness, durability of the cosmetic effect, storage stability and safety for the skin.

U.S. Pat. No. 7,820,147B2 describes a method for repairing the strength of damaged or chemically treated hair through composition containing acrylic or methacrylic acid, a wetting agent and a thickening agent that increases the viscosity of the hair restorative composition before application.

The international application WO2009024937A2 describes a method for treating damaged hair by applying shampoos comprising from 5 to 50% by weight of anionic surfactant, from 0.025 to 5% by weight of cationic polymers, preferably acrylic derivatives of diallyl dimethyl ammonium chloride, and water. Said composition of anionic surfactants and cationic polymers is said to form lyotropic liquid crystals and increase the deposition of silicones.

The application WO2011139265A2 describes a method of treating damaged hair through composition containing aminosilicone in an oil-in-water emulsion, having good thermal protection, lubricity, leaving the hair with non-oily shiny appearance, lower frizzy appearance and greater break strength.

WO2010118925A2 describes a process of treating damaged hair using compositions comprising cationic polymers, preferably double modified guar hydroxypropyltrimonium chloride, and oils (minerals, vegetables, silicones and mixtures thereof), applied to shampoos, with selective deposition of silicone to damaged sites.

CN1633959A describes a conditioning composition comprising fatty alcohols, tertiary amidoamines, silicones, glycols and other additives to obtain better combability of damaged hair.

EP3495024A1 describes a cosmetic composition containing a combination of polymers, preferably modified polyurethane with sodium sulfonate groups, with polyquaternium-39 or polyquaternium-51, and water. The composition may also optionally contain a cationic polymer, among them the polyquaternium-7, polyquaternium-10, among others. Such a composition is called a keratinocyte substrate conditioner and can be applied to cleaning products and personal care, such as shampoos and conditioners, supported by deposition, combability and sensory panel tests.

WO2019177925A1 describes a detergent composition, preferably for use in foaming cleaners, comprising non-polar oils, anionic surfactants, preferably fatty acid soap, and amphiphilic polymers. Additionally, the composition may contain a cationic polymer selected from the polyquaternium group.

In the above-mentioned patents or applications, it is stipulated that cosmetic compositions for repair of damaged hair are comprised of fatty esters, vegetable and mineral oils, modified silicones and polymers of cationic, amphoteric or anionic character, as well as mixtures thereof. Although these studies have contributed to improvements in hair attributes, such as combability, handling, luster and silicone deposition, the available alternatives do not include solutions for reducing cuticle damage and reducing protein mass loss of strands. These benefits are relevant for hair repair, since the surface of the cuticles expresses the degree of damage of the strands, which impacts on the attributes of combability, handling, luster and hydrophobicity; and the protein retention expresses the health and strength of the strands. Moreover, in the vast majority of patents or applications referred to as prior art it is stipulated that cosmetic compositions are directed to a specific application and cannot be extended to a suitable application to the entire line of hair products.

The use of treatments for hair shape and color modulation is usual among consumers, and it is necessary to develop conditioning products/compositions that not only recover the strands from the damage already caused, but also give protection to additional damage. Bearing in mind that the demand for such products has increased, it is sought, therefore, the production of compositions capable of overcoming the problems pointed out in the state of the art.

SUMMARY OF THE INVENTION

In order to solve this problem, it was verified the conditioning of the hair related not only to the neutralization of negative charges of the hair, mechanism of action of cationic polymers when isolated, but also to the lubricity added by non-ionic surfactants, to the increase of the water/strand contact angle and to the reduction of protein loss by the hair strands by the lower detergent action and contribution to the substantivity added by it.

The objective of the present invention is to promote conditioning cosmetic compositions that recover the properties of a damaged hair, so that these properties present greater consumer acceptance and reflect a behavior close to that of healthy hair. Such properties include reduced cuticle damage, increased luster, break strength, hydrophobicity, protein retention, combability and overall hair manageability.

According to a first aspect, an embodiment of the present invention provides an aqueous conditioning cosmetic composition for hair comprising at least one non-ionic surfactant and at least one cationic polymer, and optionally wherein said cosmetic composition comprises at least two non-ionic surfactants and at least two cationic polymers.

According to a second aspect, the present invention provides a cosmetic product, which comprises the cosmetic composition as previously defined, and may further comprise rinseable or non-rinseable products.

According to a third aspect, the present invention provides a method of protection, especially related to protein loss and the prevention of damage to the surface of the strands; and repair of hair properties, especially luster, break strength, hydrophobicity and handling. Said method comprises the steps of applying to the hair cosmetic products containing the aqueous conditioning cosmetic composition as previously defined.

According to a fourth aspect, the present invention defines the use of a cosmetic product, especially related to the reduction of damage to the cuticles, luster increasing, break strength, hydrophobicity, protein retention, combability, and hair management.

Surprisingly, it was observed that the composition of cationic polymers with non-ionic surfactants acts as a conditioning agent of hair and significantly reduces the protein loss of the strands. Proteins are fundamental structural components for the health of the hair strands.

The mentioned aspects and embodiments of the present invention, as well as other advantages, will be more evident from the description that follows and the attached FIGURE.

BRIEF DESCRIPTION OF THE FIGURES

The detailed description presented below refers to the attached FIGURE, which:

FIG. 1 represents the images obtained by scanning electron microscopy (SEM) of damaged hair strands with and without influence of the conditioning cosmetic composition, corresponding to fractures, fragments and elevations of the cuticles, where the strands in left hand vertical column were untreated and the strands in the right hand vertical column were treated as described herein, and where the strands in the top lateral row were bleached and the strands in the bottom lateral row were both bleached and abraded as described herein.

DETAILED DESCRIPTION OF THE INVENTION

The present invention is intended to provide conditioning cosmetic compositions for protection and repair of the properties of a damaged hair, more susceptible to future damage.

The conditioning cosmetic composition, object of this invention, acts in reducing damage to the cuticles, increasing the luster, break strength, hydrophobicity, protein retention, combability, and hair management.

The conditioning cosmetic composition, object of this invention, comprises the combination of at least one cationic polymer and a non-ionic surfactant, and in other variations at least two cationic polymers and two non-ionic surfactants.

In one of the embodiments of the aqueous conditioning cosmetic composition for hair, the at least one non-ionic surfactant is selected from the group consisting of condensation products of fatty alcohols or saturated, unsaturated or β-hydroxy-unsaturated primary or secondary fatty acids with ethylene oxide.

In particular embodiments, the at least one non-ionic surfactant comprises ethoxylated fatty alcohols having structure compatible with formula (I), wherein a and b represent the range of carbon atoms and the range of repeating units of ethylene oxide, respectively.

Formula (I)

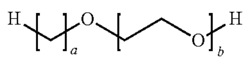

wherein a corresponds to the range of 6 to 24 carbon atoms, more specifically of 8 to 18; and b corresponds to the range of 20 to 100 units of ethylene oxide, more specifically of 25 to 85.

Examples of non-ionic surfactants: capreth-10, deceth-3, laureth-3, laureth-4, laureth-5, laureth-6, laureth-7, laureth-8, laureth-9, laureth-10, laureth-12, laureth-23, isodeceth-6, isodeceth-8, isodeceth-10, isodeceth-12, isotrideceth-6, isotrideceth-8, isotrideceth-9, $C_{9-11}$ pareth-6, $C_{9-11}$ pareth-8, myristeth-3, ceteth-20, ceteth-25, ceteth-40, ceteth-50, ceteth-80, ceteareth-20, ceteareth-25, ceteareth-40, ceteareth-50, ceteareth-60, ceteareth-80, ceteareth-100, steareth-20, steareth-40, steareth-80, cetoleth-10, cetoleth-25, cetoleth-30, PEG-15 castor oil, PEG-20 castor oil, PEG-25 castor oil, PEG-25 hydrogenated castor oil, PEG-30 castor oil, PEG-36 castor oil, PEG-40 castor oil, PEG-40 hydrogenated castor oil, PEG-54 castor oil, PEG-100 stearate, and oleth-20.

The at least one non-ionic surfactant is then combined with at least one cationic polymer, which comprises, in certain embodiments, the polyquaterniums class of structure compatible with the formulas (II) and (III), wherein n corresponds to the range of 725 to 4,600 repeating units of hydroxyethyl cationic cellulose, so that n is large enough so the aqueous solution of 2% of this polymer has viscosity between 200 and 900 mPa·s and molar mass between 250 and 900 kDa; x corresponds to the range of 3,000 to 18,500 repetition units of 2-methacryloyloxyethyl phosphorylcholine and y corresponds to the range of 750 to 5,000 repetition units of butyl methacrylate, so that x and y are large enough for this copolymer to present molar mass between 10,000 and 60,000 kDa.

Formula (II)

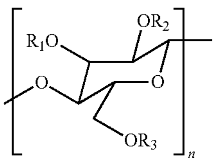

Formula (III)

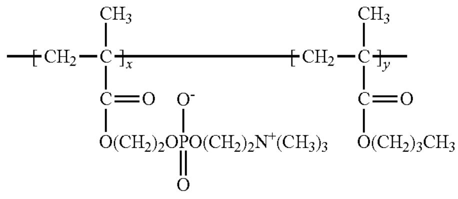

The cationic polymer of structure compatible with the formula (II) is a modification of hydroxyethyl cellulose, characterized in that $R_1$, $R_2$, and $R_3$ are selected independently from the groups —H and —$(CH_2CH_2O)_mQ$, wherein in is in the range of 1 to 5 units of ethylene oxide, and Q is a cationic group of structure compatible with the formula (IV), so that they can be chosen from 225 to 1,500 —$(CH_2CH_2O)_mQ$ groups by molecule of the polymer to a charge density or contents of nitrogen between 0.8 and 2.2%.

Formula (IV)

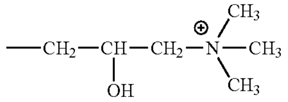

Examples of the polymers cationic: polyquaternium-4, polyquaternium-6, polyquaternium-7, polyquaternium-10, polyquaternium-11, polyquaternium-51, polyquaternium-61, polyquaternium-64, polyquaternium-65, polyquaternium-67, and polyquaternium-76.

With regard to the aqueous conditioning cosmetic composition for hair, non-ionic surfactants and cationic polymers are combined with each other in a ratio of 99:1 to 80:20 by weight or 95:5 to 90:10 by weight.

In certain embodiments, the at least one non-ionic surfactant and at least one cationic polymer are solubilized in water in the ratio of 50:50 to 20:80 by weight.

The present invention also refers to rinseable and non-rinseable products cosmetic products containing said cosmetic composition, being them, shampoos, conditioners, masks or treatment products, combing creams, ampoules, serums, mists or finishing products, among others; as well as the method of repair and protection of damaged hair, comprising the steps of application to the hair of cosmetic products containing said conditioning cosmetic composition.

Regarding the cosmetic product, it comprises from 0.2% to 10.0% by weight of the cosmetic composition, and may optionally include surfactants, emollients, emulsifiers, thickeners, preservatives, fragrances, pH regulators, water, among others.

Concrete but non-limiting examples of formulations of hair products containing the conditioning cosmetic composition illustrating the present invention are provided below.

EXAMPLES

TABLE 1

Examples of formulations of hair products containing the conditioning cosmetic composition

| Ingredient | Shampoo (I) | Shampoo (II) | Conditioner (I) | Conditioner (II) | Mask (I) | Combing cream (I) | Ampoule (I) |
|---|---|---|---|---|---|---|---|
| (Conditioning cosmetic composition) | 2.0% | 2.0% | 1.0% | 2.0% | 2.0% | 1.0% | 2.0% |
| Sodium Laureth Sulfate | 9.0% | 9.0% | — | — | — | — | — |
| Cocoamidopropyl Betaine | 2.5% | 2.5% | — | — | — | — | — |
| Cetearyl Alcohol | — | — | 4.0% | 4.0% | 4.0% | 3.0% | 5.0% |
| Ceteareth-20 | — | — | — | 0.3% | — | — | — |
| Sorbitan Laurate | — | — | — | — | 0.4% | — | — |

TABLE 1-continued

Examples of formulations of hair products containing the conditioning cosmetic composition

| Ingredient | Shampoo (I) | Shampoo (II) | Conditioner (I) | Conditioner (II) | Mask (I) | Combing cream (I) | Ampoule (I) |
|---|---|---|---|---|---|---|---|
| Decyl Glucoside | — | — | — | — | 0.5% | — | — |
| Behentrimonium Chloride | — | — | 2.0% | 0.8% | 0.8% | 0.8% | 0.8% |
| Paraffinum Liquidum (Mineral Oil) | — | — | — | 1.0% | — | — | — |
| Dimethicone | — | 0.5% | — | — | — | — | — |
| Amodimethicone | — | — | — | — | — | 0.5% | — |
| Isoamyl Cocoate | — | — | — | — | 1.0% | — | — |
| Guar Hydroxypropyl-trimonium Chloride | — | 0.2% | — | 0.2% | — | — | — |
| Sorbeth-450 Triestearate (and) PEG-9 Cocoate (and) PEG-32 Distearate (and) PEG-175 Distearate | — | — | — | — | — | — | 4.0% |
| Sodium Laureth Sulfate (and) Glycol Distearate (and) Cocamide DEA | — | 2.0% | — | — | — | — | — |
| Aloe Vera Leaf Extract | — | — | — | — | 1.0% | — | — |
| Hydrolyzed Wheat Protein | — | — | — | — | 0.5% | — | 0.5% |
| Glycerin | — | — | — | 0.1% | 0.2% | — | — |
| (Preservative) | q.s.p. | q.s.p. | q.s.p. | q.s.p. | q.s.p. | q.s.p. | q.s.p. |
| (Fragrance) | q.s.p. | q.s.p. | q.s.p. | q.s.p. | q.s.p. | q.s.p. | q.s.p. |
| (pH regulator) | q.s.p. | q.s.p. | q.s.p. | q.s.p. | q.s.p. | q.s.p. | q.s.p. |
| Aqua | q.s.p. | q.s.p. | q.s.p. | q.s.p. | q.s.p. | q.s.p. | q.s.p. |

The method of protection and repair of hair properties comprises the step of applying to the hair the cosmetic products containing the conditioning cosmetic composition as previously defined.

Conditioning agents, with continuous use in hair products, can result in the phenomenon called build-up, which is an excessive deposition of the conditioning agents in the hair perceived by the consumer as heavy and dirty hair. The composition in question, because it presents a synergistic effect between the components of the mixture, allows the benefit of conditioning to be achieved without excess deposition (build-up), widely associated with the use of silicones and their derivatives.

The hair conditioning can be perceived by the consumer through such attributes as softness, luster, less breakage of the strands and ease of combing. The conditioning composition in question acts more holistically when compared to the known state of the art, because it acts not only in the recovery of damaged strands, but also in the protection of the strands from new aggressions. The improvement in hair attributes was determined by instrumental methods and validated according to the perception of the final consumer of the product (shampoo and conditioner). Validation was carried out through the evaluation of experts in the application of hair care products and by volunteers with hair damaged by chemical treatment (bleaching). Aspects such as luster, combability, moisturization, softness, mechanical strength, increased contact angle, strength against breakage testify to the conditioning of the strands.

Efficacy Tests

The hair hydrophobicity (Table 2) can be quantified by the interaction between the hair and water through the contact angle between the water/hair and water/air interfaces. The higher the contact angle, the lower the interaction of water with the hair and the more hydrophobic is its surface. The contact angle was measured by the method of Wilhelmy, in which the Caucasian hair strands type III damaged by bleaching, without treatment, and treated with a 10% aqueous solution of the conditioning cosmetic composition, are immersed in 1.2 mm from the surface of the water, at a rate of 2.5 min/min by the mechanical arm of a force tensiometer (Krüss K 100, Germany) in order to measure the force required to detach a hair from the water.

TABLE 2

Performance of the conditioning cosmetic composition in different attributes.

| Attribute | Without Treatment | Treated with the Conditioning Cosmetic Composition |
|---|---|---|
| Hydrophobicity (°) | 41 ± 4 | 59 ± 1 |
| Cuticle damage (% pixel) | 21.0 ± 0.5 | 18.9 ± 0.3 |
| Cuticle damage after abrasion (% pixel) | 22.1 ± 0.9 | 20.0 ± 0.9 |
| Abrasion resistance after conditioner (# breaks) | 3.3 ± 0.5 | 0.8 ± 0.8 |
| Abrasion resistance after combing cream (# breaks) | 5.3 ± 0.5 | 2.0 ± 0.0 |
| Luster (BNT luster units) | 31.5 ± 1.8 | 33.8 ± 2.6 |
| Protein loss (wt %) | 0.61 ± 0.09 | 0.25 ± 0.06 |
| Maximum strength for combing after shampoo (N) | 15.60 ± 5.22 | 7.11 ± 1.64 |
| Maximum strength for combing after full regime (N) | 6.90 ± 1.24 | 0.25 ± 0.06 |

Cuticle damage (Table 2) is quantified from scanning electron microscopy (Zeiss DSM 940 a, Germany) at 15 kV and 750× of hair strands with and without treatment. The treatment consists of application of shampoo (I) and conditioner (I), conditioning the samples at 22° C. and 55% relative humidity (RH). The procedure is performed on Caucasian Type III strands damaged by bleaching and covered with 90 Å of gold (Balzers SCD 050 Sputter Coater, Liechtenstein), in order to confer the restructuring potential, i.e. the ability to repair the damage to the cuticles, as well as on strands damaged and treated after the abrasion of 1,500 automated combing strokes (Bioluz BLPA 101, Brazil), to confer the protection of the cuticles from damage.

Micrographs of damaged hair strands with and without influence of the conditioning cosmetic composition (FIG. 1) are graphically treated (Scion Image, United States) to quantify the area, in pixels, corresponding to fractures, fragments and elevations of the cuticles.

The strength of the strands was measured by abrasion resistance (Table 2), wherein strands of 3 g and 25 cm long Caucasian Type III hair, with and without treatment, were subjected to 10,000 automated combing strokes (Bioluz BLPA 101, Brazil), manually assessing the number of breakages. The lower this number, the higher the hair's resistance to breakage. The treatment was performed independently with conditioner (II) and combing cream (I), conditioning the samples at 22° C. and 55% RH.

The luster (Table 2) of the hair was instrumentally quantified (Samba Hair, United States) in strands of 2 g and 20 cm long Caucasian hair type III, before and after 6 cycles of washing with shampoo (I).

Protein retention is quantified from the amount of protein extracted from the strands, i.e. protein loss (Table 2) by Lowry's colorimetric method. Locks of Caucasian hair type III of 0.5 g were bleached and subjected to 10 cycles of washing with conditioner (II). The locks of hair were incubated in water at 50° C. and 300 rpm for 4 h. To each 1 mL of the solution containing the extracted proteins was added 0.9 mL of a mixture of tartrate 7 mM/carbonate 0.81 m/NaOH 0.5 m, incubating at 50° C. for 10 min. To this portion was added 0.1 mL of a mixture of tartrate 70 mm/$Cu^{2+}$ 40 mM, incubating at 50° C., for 10 min. To this portion were added 3 mL of a 10% solution (v/v) of Folin-Ciocalteau 2 M, incubating for 10 min and performing and reading the absorbance at 750 nm in UV-Visible Spectrophotometer (Varian Cary 1E, United States). Through an analytical curve of BSA, the absorbance value is correlated with protein concentration through Lambert-Beer law.

The instrumental combability (Texturometer Stable Micro Systems TA.XT, UK) is equivalent to the maximum combing force (Table 2), sliding the comb from the root to the tips of a strand of 3 g and 25 cm long Caucasian hair type III, before and after treatment. The treatment was performed independently with Shampoo (I) and with a regimen that consisted of Shampoo (I) followed by Conditioner (I) and Combing cream (I). The management of the strands depends not only on combability, but on a holistic assessment of other hair attributes (Table 3), conducted from sensory analysis with 10 female volunteers, aged 49±8 years, conditioned for 48 hours without the use of hair products. The performed treatment consisted of a Shampoo (I) and Conditioner (I) regimen with massage for 1 min, action for 1 min, rinse for 1 min, use of dryer and finishing with the Combing cream (I).

TABLE 3

Approval rates after treatment with conditioning cosmetic composition.

| | Professional assessment | | Perception of volunteers | |
|---|---|---|---|---|
| Attribute | Wet Hair | Dry Hair | Wet Hair | Dry Hair |
| Luster | 100% | 100% | 90% | 90% |
| Conditioning | 100% | 100% | 100% | 100% |
| Hydration | 100% | 70% | 100% | 100% |
| Softness | 100% | 90% | 100% | 100% |
| Ease in combing | 100% | 100% | 100% | 90% |
| Smooth touch | 100% | 80% | 100% | 100% |

The description recited so far of the object of the present invention should be considered only as possible embodiments and/or achievements, and any particular characteristics introduced therein should be understood only as something that has been written to facilitate comprehension. Thus, it should not be considered as limiting the invention, which is limited to the scope of the claims that follow.

The invention claimed is:

1. An aqueous conditioning cosmetic composition for hair, characterized by comprising:

at least one non-ionic surfactant comprising ethoxylated fatty alcohols having structure compatible with formula (I), wherein a and b, respectively, ranges from 6 to 24 carbon atoms and ranges from 20 to 100 units of ethylene oxide Formula (I)

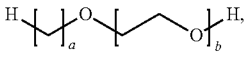

and at least one cationic polymer which belongs to the polyquaterniums class of structure compatible with the formulas (II) and (III) wherein n corresponds to the range of 725 to 4,600 repeating units, being n large enough for the aqueous solution of 2% of this polymer to have viscosity between 200 and 900 mPa·s and molar mass between 250 and 900 kDa; x and y correspond, respectively, to the ranges of 3,000 to 18,500 and of 750 to 5,000 repetition units, being x and y large enough so that the polymer has molar mass between 10,000 and 60,000 kDa, Formula (II)

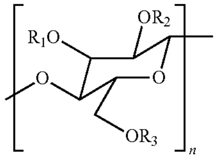

wherein the formula (II) consists of $R_1$, $R_2$ e $R_3$ independently chosen between the groups —H and —$(CH_2CH_2O)_mQ$, wherein m corresponds to the range of 1 to 5 units of ethylene oxide and Q is a cationic group of structure compatible with the Formula (IV), so that the charge density and nitrogen content are in the range of 0.8% to 2.2%

Formula (III)

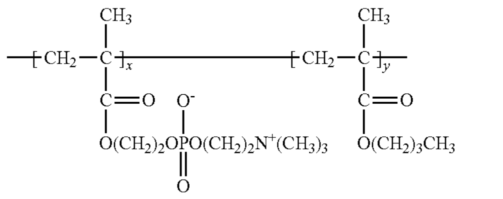

Formula (IV)

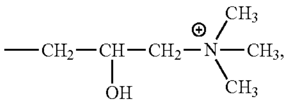

wherein the at least one non-ionic surfactant and the at least one cationic polymer are combined with each other in a ratio between their totalities from 99:1 to 80:20 by weight, and wherein the composition is free of silicones, including aminated silicones.

2. The aqueous conditioning cosmetic composition for hair according to claim 1, characterized by comprising at least two non-ionic surfactants and at least two cationic polymers.

3. The aqueous conditioning cosmetic composition for hair according to claim 1, characterized in that at least one non-ionic surfactant is selected from the group consisting of condensation products of fatty alcohols or saturated, unsaturated or β-hydroxy-unsaturated primary or secondary fatty acids with ethylene oxide.

4. The aqueous conditioning cosmetic composition for hair according to claim 1, wherein a ranges from 8 to 18 carbon atoms.

5. The aqueous conditioning cosmetic composition for hair according to claim 1, wherein b ranges from 25 to 85 units of ethylene oxide.

6. The aqueous conditioning cosmetic composition for hair according to claim 1, characterized in that the at least one non-ionic surfactant and the at least one cationic polymer are combined with each other in a ratio between their totalities from 95:5 to 90:10 by weight.

7. The aqueous conditioning cosmetic composition for hair according to claim 1, characterized in that the at least one non-ionic surfactant and the at least one cationic polymer are solubilized in water, wherein they are together in the ratio of 50:50 to 20:80 by weight with respect to water.

8. A cosmetic product, characterized by comprising the cosmetic composition as defined in claim 1.

9. The cosmetic product according to claim 8, characterized by comprising from 0.2% to 10.0% by weight of the cosmetic composition.

10. The cosmetic product according to claim 8, characterized by comprising rinsible cosmetic products for hair care or non-rinsible cosmetic products for hair care.

11. The cosmetic product according to claim 10, characterized by the said rinsible cosmetic products for hair care are selected from the group consisting of shampoos, conditioners, masks or treatment products; and said non-rinsible cosmetic products for hair care are selected from the group consisting of creams for combing, treatment products, ampoules, serums, mists or finishing products.

12. A method of repair and protection of hair, acting in the reduction of damage to the cuticles, increasing of luster, resistance to breakage, hydrophobicity, protein retention, combability, and hair manageability, characterized by comprising the step of applying to the hair cosmetic products as defined in claim 8.

* * * * *